US005955599A

United States Patent [19]
Iyer et al.

[11] Patent Number: 5,955,599
[45] Date of Patent: *Sep. 21, 1999

[54] PROCESS FOR MAKING OLIGONUCLEOTIDES CONTAINING O- AND S- METHYLPHOSPHOTRIESTER INTERNUCLEOSIDE LINKAGES

[75] Inventors: Radhakrishnan P. Iyer, Shrewsbury; Theresa Devlin, Jamaica Plain; Ivan Habus, Shrewsbury; Dong Yu, Shrewsbury; Sudhir Agrawal, Shrewsbury, all of Mass.

[73] Assignee: Hybridon, Inc., Milford, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/570,390

[22] Filed: Dec. 11, 1995

Related U.S. Application Data

[63] Continuation-in-part of application No. 08/457,198, Jun. 1, 1995, abandoned.

[51] Int. Cl.⁶ .................................................. C07H 21/04
[52] U.S. Cl. ...................... 536/25.3; 536/23.1; 435/91.1; 435/442
[58] Field of Search .................. 536/23.1, 24.5, 536/25.3, 24.33, 24.3; 514/44, 48; 435/6, 375, 91.1, 442, 372

[56] References Cited

U.S. PATENT DOCUMENTS

| | | | |
|---|---|---|---|
| 5,149,798 | 9/1992 | Agrawal et al. | 536/25.3 |
| 5,264,566 | 11/1993 | Froehler et al. | 536/25.34 |

OTHER PUBLICATIONS

Debenham et al. (1995) *Journal of the American Chemical Society* 117:3302–3303.
Iyer et al. (1995) *Journal of Organic Chemistry* 60:8132–8133.
Madsen et al. (1995) *Journal of Organic Chemistry* 60:7920–7926.
Agrawal et al. (1993) *Methods in Molecular Biology* 20:165–189.
Agrawal et al. (1995) *Curr Op in Biotech* 6:12–19.
Khorona et al. (1972) *J. Molec. Biol.* 72:209–217.
Henry et al. (1994) *Phar. Res.* 11:PPDM8082.
Beaucage et al. (1981) *Tetrahedron Letters* 22:1859–1862.
Agrawal et al. (1987) *Tetrahedron Letters* 28:3539–3542.
Connolly et al. (1984) *Biochemistry* 23:3443–3453.
Jager et al. (1988) *Biochemistry* 27:7237–7246.
Agrawal et al. (1988) *Proc. Nat. Acad. Sci. (USA)* 85:7079–7083.
Galbraith et al. (1994) *Antisense Research and Development* 4:201–206.
Miller et al. (1971) *J. Am. Chem. Soc.* 93:6657–6665.
Moody et al. (1989) *Nucleic Acids Res.* 17:4769–4783.
Miller et al. (1983) *Tetrahedron Letters* 24:245–248.
Buck et al. (1990) *Science* 248:208–212.
Buck et al. (1990) *Science* 249:125–126.
Alul et al. (1991) *Nucl. Acids Res.* 19:1527–1532.
Kuijpers et al. (1990) *Nucl. Acids Res.* 18:5197–5205.
Vinogradov et al. (1993) *Tetrahedron Letters* 34:5899–5902.
Hayakawa et al. (1995) *J. Org. Chemistry* 60:925–930.
Iyer et al. (1995) *Tetrahedron Asymetry* 6:1051–1054.
Beaucage et al. (1992) *Tetrahedron* 48:2223–2311.
Pon (1993) *Methods in Molecular Biology* 20:465–497.
Beaucage et al. (1993) *Methods in Molecular Biology* 20:33–61.
Agrawal et al. (1992) *Antisense Research and Development* 2:261–266.
E. Uhlmann et al. Chem. Rev. 90 (4):543–84 (1990).
J. Milligan et al. J. Med. Chem. 36(14) 1923–37 (1993).
C. Stein et al. Science 261:1004–12 (1993).
B. Tseng et al. Cancer Gene Therapy 1(1) 65–71 (1994).
R. Stoll et al. Pharmaceut. Res. 12(4):465–83 (1995).
P. Quaedflieg et al. J. Org. Chem. 56:5846–59 (1991).
K. Yamana et al. Tetrahedron Lett. 32(36) 4721–24 (1991).

*Primary Examiner*—John L. LeGuyader
*Attorney, Agent, or Firm*—Hale and Dorr LLP

[57] ABSTRACT

The invention provides oligonucleotides containing methyl phosphotriester linkages and processes for making and methods for using such oligonucleotides.

14 Claims, 4 Drawing Sheets

PROCESS FOR MAKING OLIGONUCLEOTIDES CONTAINING O- AND S- METHYLPHOSPHOTRIESTER INTERNUCLEOSIDE LINKAGES

This is a continuation-in-part of U.S. Ser. No. 08/457,198, filed Jun. 1, 1995, now abandoned.

BACKGROUND OF THE INVENTION

1. Field of the Invention

The invention relates to synthetic oligonucleotides and to their use in molecular biology applications and in the antisense therapeutic approach.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Carruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager el al., *Biochemistry* 27: 7237 (1988), discloses synthesis of oligonucleotide phosphoramidates using phosphoramidite chemistry. Agrawal et al., *Proc. Natl. Acad. Sci. USA* 85: 7079–7083 (1988), discloses synthesis of oligonucleotide phosphoramidates and phosphorothioates using H-phosphonate chemistry.

The routine synthesis of oligonucleotides is presently carried out using various N-acyl protecting groups for the nucleoside bases, such as isobutyryl (for guanine), and benzoyl for adenine and cytosine. After the synthesis of the oligonucleotides is carried out using either phosphoramidite chemistry or H-phosphonate chemistry, the protecting groups are removed by treatment with ammonia at 55–60° C. for 5–10 hours. Using these protecting groups, PO oligonucleotides and other modified oligonucleotides can be synthesized. But in certain instances where modified oligonucleotides are functionalized with base-sensitive groups, the functionalities often get removed while the deprotection is being carried out.

This limitation in the oligonucleotide synthesis procedure has resulted in the inability to synthesize certain modified oligonucleotides that may have considerable utility. For example, oligonucleotides containing methyl phosphotriester internucleotide linkages could have many beneficial properties, because the methyl phosphotriester group is nonionic, but is similar in size and molecular shape to the phosphodiester linkage. Such nonionic methyl phosphotriester linkages could result in a reduction in oligonucleotide side effects that are attributable to the polyanionic character of the oligonucleotides. For example, Galbraith et al., Antisense Research and Development 4: 201–206 (1994) disclose complement activation by oligonucleotides. Henry et al., Pharm. Res. 11: PPDM8082 (1994) discloses that oligonucleotides may potentially interfere with blood clotting.

The art has recognized the desirability of incorporating methyl phosphotriester internucleotide linkages into oligonucleotides and many attempts have been made to make and use such oligonucleotides. However, these attempts have subsequently been discovered to be unsuccessful. Miller et al., J. Am. Chem. Soc. 93: 6657–6665 (1971), discloses alleged methylphosphotriester DNA synthesis by methylation of the phosphate using p-toluenesulphonyl chloride and methanol. Moody et al., Nucl. Acids Res. 17: 4769–4783 (1989), discloses regiospecific inhibition of DNA duplication by oligonucleotides synthesized according to the method of Miller et al.. Buck et al., Science 248: 208–212 (1990), discloses that oligonucleotides according to Moody et al. inhibit viral infectivity of HIV-1. However, Buck et al., Science 249: 125–126 (1990), retracts the earlier Buck et al. report and discloses that oligonucleotides synthesized according to this method do not contain methyl phosphotriester internucleotide linkages.

The difficulty in synthesizing oligonucleotides having methyl phosphotriester internucleotide linkages is due to the lability of the methyl ester bond under the oligonucleotide synthesis conditions used in the steps of deprotecting the nucleoside bases and cleaving the oligonucleotides from the solid support. Alul et al., Nucl. Acids Res. 19: 1527–1532 (1991), addressed the problem of cleaving the oligonucleotide from the solid support by introducing an oxalyl-type linker that can be cleaved under conditions that preserve the methyl ester bond. However, the problem of base deprotection was not addressed, so they were only able to synthesize methyl phosphotriester-linked thymidines, which lack an exocyclic amino group and thus do not require deprotection. Kuijpers et al., Nucl. Acids Res. 18: 5197–5205 (1990), attempted to address the deprotection problem by treating the nucleoside bases for 43 hours in potassium carbonate/methanol. Unfortunately, NMR analysis of their oligonucleotides revealed that considerable demethylation had occurred, resulting oligonucleotides having a mixture of methylphosphotriester and phosphodiester linkages. Similarly, Vinogradov et al., Tetrahedron Lett. 34: 5899–5902 (1993), attempted to solve the problem by using an isopropoxyacetyl group to protect the nucleoside bases, but found that at least 35–40% demethylation still occurred. Most recently, Hayakawa et al., J. Org. Chem. 60: 925–930 (1995), claimed to have synthesized a decamer oligonucleotide containing a single methyl phosphotriester internucleotide linkage. However, NMR data supporting this claim was absent. Moreover, the method employed utilized costly and toxic palladium, which could contaminate the oligonucleotide product and render it unsuitable for therapeutic applications. In addition, the method was not shown to be able to introduce multiple methylphosphotriester linkages into the oligonucleotide.

There is therefore, a need for oligonucleotides containing methyl phosphotriester internucleotide linkages, as well as for new methods for synthesizing such oligonucleotides. Ideally, such oligonucleotides should be easy to synthesize and should be capable of containing numerous other beneficial modifications.

BRIEF SUMMARY OF THE INVENTION

The invention provides oligonucleotides containing methyl phosphotriester internucleotide linkages and processes for making and methods for using such oligonucleotides. The oligonucleotides according to the invention are easy to synthesize and can conveniently be made to contain numerous other beneficial modifications.

In a first aspect, the invention provides oligonucleotides containing methyl phosphotriester internucleotide linkages having the structure I:

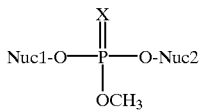

wherein "Nuc1" represents the 3' position of a first nucleoside, "Nuc2" represents the 5' position of a second nucleoside, and X represents sulfur or oxygen. The linkage provides the benefit of having a molecular size that is similar to that of a natural phosphodiester linkage, but at the same time having nonionic character. Such an internucleoside linkage should confer upon an oligonucleotide a reduction in polyanion-mediated side effects and should also improve cellular uptake of the oligonucleotide.

Oligonucleotides according to this aspect of the invention have from one to about all internucleotide linkages in the form of methyl phosphotriester linkages. In embodiments of oligonucleotides according to this aspect of the invention that have fewer than all methyl phosphotriester internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible.

Oligonucleotides containing such a mixture of internucleoside linkages are referred to herein as mixed backbone oligonucleotides. In some preferred embodiments of mixed backbone oligonucleotides according to the invention, the internucleoside linkages that are not methyl phosphotriester linkages are selected from the group consisting of phosphodiester, alkylphosphonate, carbamate and phosphorothioate internucleoside linkages. In some preferred embodiments of mixed backbone oligonucleotides according to the invention, several adjacent nucleosides comprising one region of the oligonucleotide are connected by methyl phosphotriester linkages, and several other adjacent nucleosides comprising another region of the oligonucleotide are connected by a different type of internucleoside linkage. These preferred oligonucleotides are referred to herein as "chimeric" oligonucleotides. Oligonucleotides according to the invention are useful for a variety of purposes. For example, they can be labelled with a reporter group and used as probes in conventional nucleic acid hybridization assays. They can also be used as antisense "probes" of specific gene function by being used to block the expression of a specific gene in an experimental cell culture or animal system and to evaluate the effect of blocking such specific gene expression. In this use, oligonucleotides according to the invention are preferable to traditional "gene knockout" approaches because they are easier to use and can be used to block specific gene expression at selected stages of development or differentiation. Finally, oligonucleotides according to the invention are useful in the antisense therapeutic approach. In this use, oligonucleotides according to the invention should have reduced polyanion-mediated side effects and improved cellular uptake.

In a second aspect, the invention provides a simple process for synthesizing an oligonucleotide containing from one to about all methyl phosphotriester internucleoside linkages. This process comprises condensing in the presence of 1H-tetrazole a methoxy-3'O-(phosphoramidite)-5'-O-(4, 4'-dimethoxytriphenyl)methyl nucleoside with another nucleoside, wherein at least one of the nucleosides has a nucleoside base-protective group, to produce adjacent nucleosides coupled by a phosphite linkage, wherein at least one of the nucleosides has a nucleoside base-protective group, oxidizing the internucleotidic phosphite linkage, and chemoselectively removing the nucleoside base-protective group without demethylating the methyl phosphotriester linkage(s). In one preferred embodiment, the process according to this aspect of the invention is carried out on a solid support and in a most preferred embodiment further comprises the step of cleaving the oligonucleotide from a solid support without demethylating the methyl phosphotriester linkage(s). This process allows for synthesis of oligonucleotides containing methyl phosphotriester internucleoside linkages, because the process utilizes a new nucleoside base protective group that can be chemoselectively removed, in contrast to the harsh deprotective conditions utilized by known methods, which would demethylate the sensitive methyl phosphotriester linkage. Importantly, the process according to the invention is compatible with and can be used in conjunction with any of the well known oligonucleotide synthetic chemistries, including the H-phosphonate, phosphoramidite and phosphotriester chemistries. Consequently, the process according to the invention can be used to synthesize oligonucleotides having methyl phosphotriester linkages at some internucleoside positions and other linkages at other internucleoside positions.

DETAILED DESCRIPTION OF THE PREFERRED EMBODIMENTS

Figure 1:
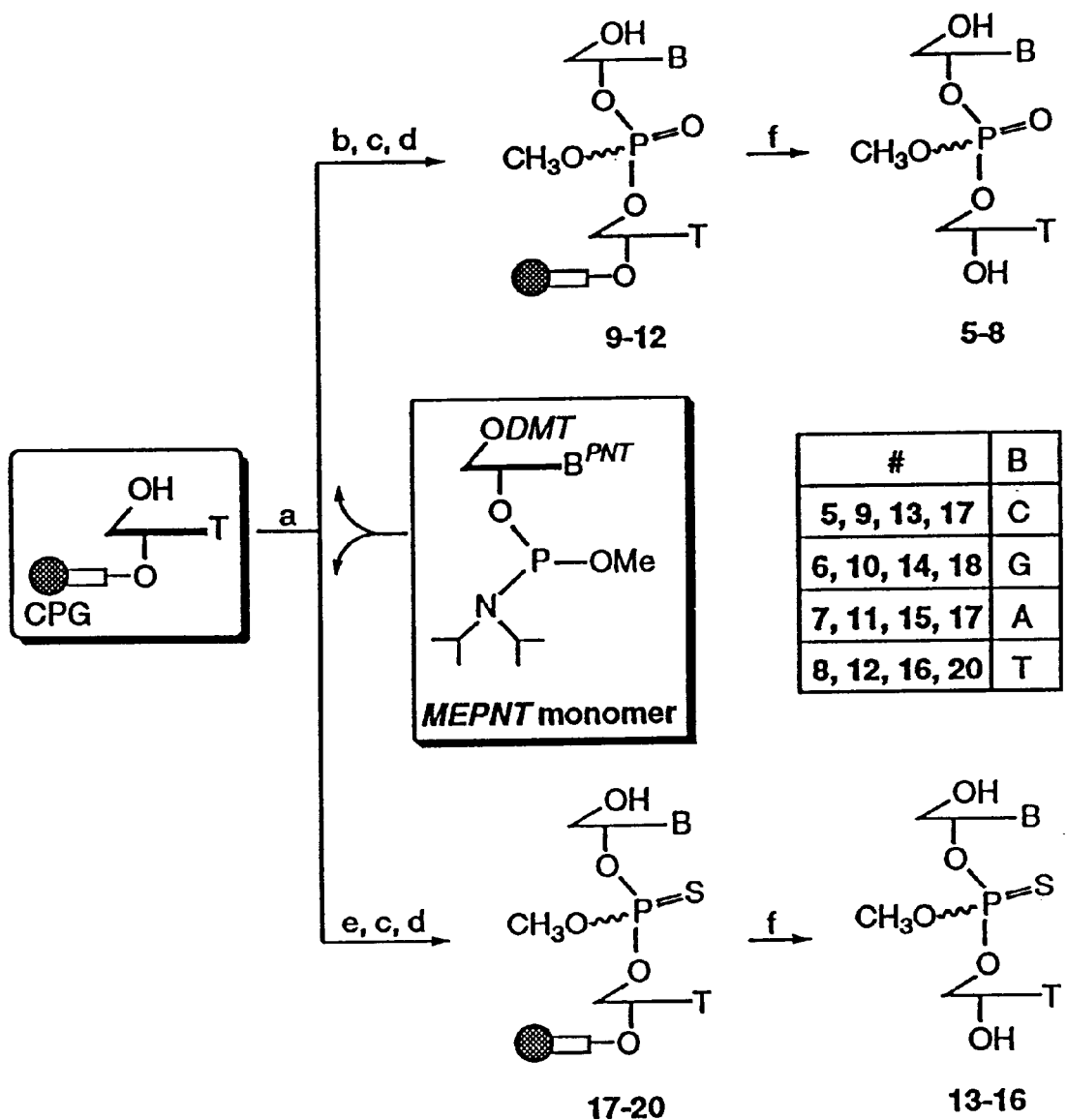
FIG. 1 shows a scheme for a preferred embodiment of a process for synthesis of an oligonucleotide containing O- or S-methyl phosphotriester internucleoside linkages. In this scheme, a) is 1H-tetrazole; b) is t-BuOOH (1 M in toluene); c) is DCA/DCM; d) is $I_2$ (2% in Pyr/MeOH 98/2); e) is 3H-benzodithiol-3-one 1,1-dioxide; and f) is anhyd $K_2CO_3$/MeOH (0.05 M).

The invention relates to synthetic oligonucleotides and to their use in molecular biology applications and in the antisense therapeutic approach. The patents and publications identified in this specification are within the knowledge of those skilled in this field and are hereby incorporated by reference in their entirety.

The invention provides oligonucleotides containing methyl phosphotriester linkages and processes for making and methods for using such oligonucleotides. The oligonucleotides according to the invention are easy to synthesize and can conveniently be made to contain numerous other beneficial modifications.

In a first aspect, the invention provides oligonucleotides having from one to about all internucleotide linkages in the form of a methyl phosphotriester internucleoside linkage having the structure I:

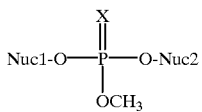

wherein "Nuc1" represents the 3' position of a first nucleoside, "Nuc2" represents the 5' position of a second nucleoside, and X is sulfur or oxygen. This structure is similar in molecular size and shape to the natural phosphodiester internucleoside linkage, and as such, should not contribute significantly to any steric constraints to the oligonucleotide. Accordingly, this internucleoside linkage should not have a significant effect on the ability of an oligonucleotide to hybridize with a complementary nucleic acid. The linkage provides the benefit of having nonionic character. Such an internucleoside linkage should confer upon an oligonucleotide a reduction in polyanion-mediated side effects and should also improve cellular uptake of the oligonucleotide.

For purposes of the invention, the term "oligonucleotide" includes polymers of two or more deoxyribonucleotide or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group(to produce a ribonucleoside), an amino or a halo group, but not with a 2'-H group.

Oligonucleotides according to the invention will preferably have from about 12 to about 50 nucleotides, most preferably from about 17 to about 35 nucleotides. Preferably, such oligonucleotides will have a nucleotide sequence that is complementary to a genomic region, a gene, or an RNA transcript thereof. The term complementary means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition. The gene sequence or RNA transcript sequence to which the modified oligonucleotide sequence is complementary will depend upon the biological effect that is sought to be modified. In some cases, the genomic region, gene, or RNA transcript thereof may be from a virus. Preferred viruses include, without limitation, human immunodeficiency virus (type 1 or 2), influenza virus, herpes simplex virus (type 1 or 2), Epstein-Barr virus, cytomegalovirus, respiratory syncytial virus, influenza virus, hepatitis B virus, hepatitis C virus and papilloma virus. In other cases, the genomic region, gene, or RNA transcript thereof may be from endogenous mammalian (including human) chromosomal DNA. Preferred examples of such genomic regions, genes or RNA transcripts thereof include, without limitation, sequences encoding vascular endothelial growth factor (VEGF), beta amyloid, DNA methyltransferase, protein kinase A, ApoE4 protein, p-glycoprotein, c-MYC protein, BCL-2 protein, protein kinase A and CAPL. In yet other cases, the genomic region, gene, or RNA transcript thereof may be from a eukaryotic or prokaryotic pathogen including, without limitation, *Plasmodium falciparum, Plasmodium malarie, Plasmodium ovale, Schistosoma spp.*, and *Mycobacterium tuberculosis*.

In embodiments of oligonucleotides according to this aspect of the invention that have fewer than all methyl phosphotriester internucleoside linkages, the other internucleoside linkages may be any of the known internucleoside linkages, or may be any internucleoside linkage not yet known that can be incorporated into an oligonucleotide according to a synthetic chemistry with which the process according to the invention is compatible. In certain preferred embodiments, the other internucleoside linkages are phosphodiester or phosphorothioate linkages. In the case of phosphorothioate internucleoside linkages, the linkages may be phosphorothioate mixed enantiomers or stereoregular phosphorothioates (see Iyer et al., Tetrahedron Asymmetry 6: 1051–1054 (1995).

Oligonucleotides containing such a mixture of internucleoside linkages are referred to herein as mixed backbone oligonucleotides. In some preferred embodiments of mixed backbone oligonucleotides according to the invention, several adjacent nucleosides comprising a first region of the oligonucleotide are connected by methyl phosphotriester linkages, and several other adjacent nucleosides comprising a second region of the oligonucleotide are connected by a different type of internucleoside linkage. These preferred oligonucleotides are referred to herein as "chimeric" oligonucleotides or "chimeras". In certain particularly preferred chimeric oligonucleotides according to the invention, the oligonucleotide comprises a methyl phosphotriester region and a phosphorothioate and/or phosphodiester region. In this context, a "methyl phosphotriester region" is a region within an oligonucleotide of from about 2 to about 15 contiguous nucleosides linked to each other through methyl phosphotriester linkages according to the invention, I. A "phosphorothioate region" is a region within an oligonucleotide of from about 4 to about 20 contiguous nucleosides linked to each other through phosphorothioate linkages. A "phosphodiester region" is a region within an oligonucleotide of from about 4 to about 20 contiguous nucleosides linked to each other through phosphodiester linkages. In most preferred chimeric oligonucleotides according to the invention, the oligonucleotide comprises a phosphorothioate or phosphodiester region flanked on either side by a methyl phosphotriester region, or alternatively, a methyl phosphotriester region flanked on either side by a phosphorothioate or phosphodiester region. In one preferred embodiment the nucleosides of one or more of the methyl phosphotriester region, the phosphodiester region and/or the phosphorothioate region are 2'-O-substituted ribonucleotides, as defined above herein. Preferred chimeric oligonucleotides according to the invention are further characterized by having the ability to activate RNaseH.

Oligonucleotides according to the invention are useful for a variety of purposes. For example, they can be labelled with a reporter group and used as probes in conventional nucleic acid hybridization assays. They can also be used as antisense "probes" of specific gene function by being used to block the expression of a specific gene in an experimental cell culture or animal system and to evaluate the effect of blocking such specific gene expression. This is accomplished by administering to a cell or an animal an oligonucleotide according to the invention that has a nucleotide sequence that is complementary to a specific gene that is expressed in the cell or animal to inhibit the expression of the specific gene, and observing the effect of inhibiting the expression of the specific gene. In this use, oligonucleotides according to the invention are preferable to traditional "gene knockout" approaches because they are easier to use and can be used to block gene specific gene expression at selected stages of development or differentiation.

Finally, oligonucleotides according to the invention are useful in the antisense therapeutic approach. In this use, oligonucleotides according to the invention should have reduced polyanion-mediated side effects and improved cellular uptake. For therapeutic use, oligonucleotides according to the invention may optionally be formulated with any of the well known pharmaceutically acceptable carriers or diluents. This formulation may further contain one or more additional oligonucleotides according to the invention. Alternatively, this formulation may contain one or more other antisense oligonucleotide, such as an oligonucleotide phosphorthioate, a RNA/DNA hybrid oligonucleotide, or a chimeric oligonucleotide containing known internucleoside linkages, or it may contain any other pharmacologically active agent.

Therapeutic use of oligonucleotides according to the invention is for treating a disease caused by aberrant gene expression. This is accomplished by administering to an individual having the disease a therapeutically effective amount of an oligonucleotide according to the invention, wherein the oligonucleotide is complementary to a gene that is aberrantly expressed, wherein such aberrant expression causes the disease. In this context, aberrant gene expression means expression in a host organism of a gene required for the propagation of a virus or a prokaryotic or eukaryotic pathogen, or inappropriate expression of a host cellular gene. Inappropriate host cellular gene expression includes expression of a mutant allele of a cellular gene, or underexpression or overexpression of a normal allele of a cellular gene, such that disease results from such inappropriate host cellular gene expression. Preferably, such administration should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may desirable to administer simultaneously, or sequentially a therapeutically effective amount of one or more of the therapeutic compositions of the invention to an individual as a single treatment episode.

In a second aspect, the invention provides a simple process for synthesizing an oligonucleotide containing from one to about all methyl phosphotriester internucleoside linkages. This process comprises condensing in the presence of 1H-tetrazole a methoxy-3'-O-(phosphoramidite)-5'-O-(4, 4'-dimethoxytriphenyl)methyl nucleoside with another nucleoside, wherein at least one of the nucleosides has a nucleoside base-protective group, to produce adjacent nucleosides coupled by a phosphite linkage, wherein at least one of the nucleosides has a nucleoside base-protective group, oxidizing the internucleotidic phosphite linkage, and chemoselectively removing the nucleoside base-protective group without demethylating the methyl phosphotriester linkage(s). In a preferred embodiment, the internucleotidic phosphite linkage is oxidized using t-butyl hydroperoxide, most preferably in toluene, to yield an O-methyl phosphotriester linkage. However, other non-iodine-based oxidizing agents are known in the art and may be used for this purpose (see e.g., Beaucage and Iyer, Tetrahedron Lett. 48: 2223 (1992). In another preferred embodiment, the internucleotidic phosphite linkage is oxidized using 3H-benzodithiol-3-one 1,1-dioxide to yield an S-methyl phosphotriester linkage. See FIG. 1. In one preferred embodiment, the process according to this aspect of the invention is carried out on a solid support and in a most preferred embodiment further comprises the step of cleaving the oligonucleotide from a solid support without demethylating the methyl phosphotriester linkage(s). This process allows for synthesis of oligonucleotides containing methyl phosphotriester internucleoside linkages, because the process utilizes a new nucleoside base protective group that can be chemoselectively removed, in contrast to the harsh deprotective conditions utilized by known processes, which would cleave the sensitive methyl phosphotriester linkage. The new nucleoside base protective group has the general structure II:

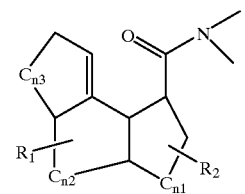

where $n_1$, $n_2$, and $n_3$ are independently 0–10, the ring structures shown may be aromatic or heterocyclic, the nitrogen displayed is the protected amino moiety of the nucleoside base, and $R_1$ and $R_2$ are independently hydrogen, or an alkyl, aryl, aralkyl, ether, hydroxy, nitrile, nitro, ester, carboxyl, or aldehyde group.

In a preferred embodiment, compound II has $n_1$, $n_2$ and $n_3$ values of 0 and thus takes the form N-pent-4-enoyl (PNT), i.e., $CH_2=CH(CH_2)_2CO-$ (III). Compounds II and III protect the nucleoside base amino moieties by forming amide linkages, as in:

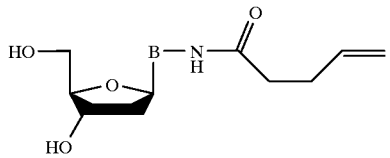

where the nitrogen displayed is the protected amino moiety of the nucleoside base B. The chemoselective removal of the nucleoside base protective group is accomplished by using a chemoselective removing agent. In certain preferred embodiments, the chemoselective removing agent is selected from the group consisting of halogens, especially $Br_2$, $Cl_2$ and $I_2$, any of which are preferably in water, or in pyridine/ROH, wherein R is an alkyl, aralkyl or aryl group having 1–10 carbon atoms, or as an N-halosuccinimide. Cleavage of the oligonucleotide from the solid support without demethylating the methyl phosphotriester internucleoside linkage is preferably carried out by treating the support bound oligonucleotide using anhydrous $K_2CO_3$, most preferably in an aprotic solvent such as methanol.

Importantly, the process according to the invention is compatible with and can be used in conjunction with any of the well known oligonucleotide synthetic chemistries, including the H-phosphonate, phosphoramidite and phosphotriester chemistries. Consequently, the process according to the invention can be used to synthesize oligonucleotides having methyl phosphotriester linkages at some internucleoside positions and other linkages at other internucleoside positions. In one preferred embodiment, synthesis is carried out on a suitable solid support using either H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)). Synthesis on such a solid support begins with coupling a nucleoside synthon according to the invention to a nucleoside that is covalently linked to the solid support (i.e., linked to a functionality on the solid support, preferably an amino or hydroxyl functionality). More generally, the process according to the invention can be used with any of the chemistries commonly used for oligonucleotide synthesis, whether in solution phase or in solid phase.

The versatility of chemical synthetic approach of the process according to the invention makes the process according to the invention suitable for the synthesis of any of a broad class of compounds, all of which are referred to herein as "oligonucleotides", as previously defined herein.

The following examples are intended to further illustrate certain preferred embodiments of the invention and are not limiting in nature.

EXAMPLE 1
Preparation of N-pent-4-enoyl(PNT) 2'-deoxy adenosine (dA Npr):

2'-Deoxyadenosine (Mallinkckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4 g, 20 mmol) was added and the contents stirred. After 15 min triethyl amine (3 ml) was added and the contents stirred for 2–3 h. The reaction slurry was cooled to 0–5° C. and 10 ml of water was added. After 5 min., 28% $NH_4OH$ (10 ml) was added. The resulting clear solution was evaporated to dryness. Water (150 ml) was added and the reaction mixture was extracted with ethylacetate: ether (50 ml, 1:1). The aqueous layer was separated and concentrated to a small volume. Upon leaving at room temperature, a white precipitate of the title compound was obtained. Filtration and drying gave ca. 3.5 g of pure title compound. Several experiments repeating the above procedure, using larger scale of operation, gave the title compound in 85–90% yield.

The same general procedure can be employed for the preparation of dG and dC protected nucleosides.

EXAMPLE 2
Preparation of 5'-O-DMT-N-4-pent-4-enoyl-nucleoside synthons

The PNT nucleosides prepared according to Example 1 were then employed in the synthesis of beta-cyanoethyl-(CEPNT) and methoxy-(MEPNT) 3'-O-(phosphoramidite)-5'-O-(4,4-dimethoxytriphenyl) methyl) [DMT] monomers according to standard procedures. See Beaucage, in *Protocols for Oligonucleotides and Analogs;* S. Agrawal, Ed.; Humana Press: Totowa, N.J. (1993); Vol. 20, pp. 33–61. The nucleoside phosphoramidites were fully characterized and the following spectral data was obtained.

MEPNT (dA). White foam; overall yield of 70–72%
$^{31}$P-NMR ($CDCL_3$): δ 147.04, 146.90 ppm (ca. $R_p:S_p$, 1:1 mixture)
$^1$H-NMR ($CDCL_3$): 8.61 (1H, s), 8.55 (1H, br), 8.17 (1H, s), 7.42–7.19 (9H, m), 6.82–6.75 (4H, m), 6.48 (1H, dd, J=2.9, 6.4 Hz), 5.93 (1H, ddt, J=6.5, 10.3, 17 Hz) 5.13 (1H, dd, J=17.0, 1.4 Hz), 5.04 (1H, dd, J=1.4, 10.3 Hz), 4.82–4.70 (1H, m), 4.38–4.28 (1H, m), 3.8 (6H, s), 3.58 (2H, m), 3.49 (2H, m, $^3J_{P-H}$=18.1 Hz, J=6.8 Hz), 3.35 (3H, d, $^3J_{P-H}$=13.4 Hz), 3.0 (2H, t, J=7.4 Hz), 2.87 (1H, m), 2.66 (1H, m), 2.53 (2H, m), 1.17 (12H, dd, J=6.8 Hz, $^4J_{P-H}$=2.4 Hz)
FAB-MS: Calcd for $C_{43}H_{53}N_6O_7P$, 797 $(M+H)^+$; Found m/z 797.

MEPNT (dC). Pale yellow foam; overall yield of 74–76%
$^{31}$P-NMR ($CDCl_3$): δ, 147.49, 146.81 ppm (ca. $R_p:S_p$, 1:1 mixture).
$^1$H-NMR ($CDCl_3$): δ 10.0 (1H, br), 8.24 (1H, d, J=7.4 Hz), 8.18 (1H, d, J=7.4 Hz), 7.40–7.08 (9H, m), 6.84–6.76 (4H, m), 6.17 (1H, dd, J=6.3, 5.1 Hz), 5.78 (1H, ddt, J=6.4, 10, 16.9 Hz), 5.02 (1H, dd, J=1.4, 17,3 HZ), 4.94 (1H, dd, J=1.4, 10.2 Hz), 4.62–4.54 (1H, m), 4.08 (1H, m), 3.61 (6H, s), 3.56–3.40 (4H, m), 3.26 (3H, d, $^3J_{P-H}$=13.2 Hz), 2.88–2.57 (3H, m), 2.40–2.34 (2H, m), 2.24–2.18 (1H, m), 1.02 (12H, d, J=6.7 Hz).
FAB-MS: Calcd. for $C_{42}H_{53}N_4O_8P$, 773 $(M+H)^+$; Found m/z, 773.

MEPNT (dG) White foam; overall yield of 70–72%
$^{31}$P-NMR ($CDCl_3$): δ 146.78, 146.74 ppm (ca. $R_p:S_p$, 1:1 mixture)
$^1$H-NMR ($CDCl_3$): δ 8.02 (1H, br), 7.92 (1H, s), 7.80 (1H, S), 7.43–7.20 (9H, m), 6.80–6.69 (4H, m), 6.20 (1H, dd, J=5.6, 7.9 Hz), 5.68 (1H, m), 4.96 (1H, dd, J=1.5, 17.1 Hz), 4.94 (1H, dd, J=1.5, 9.3 Hz), 4.72–4.63 (1H, m), 4.14–4.07 (1H, m), 3.63 (6H, s), 3.57–3.36 (4H, m), 3.29 (3H, d, $^3J_{P-H}$=13.2 Hz), 3.08 (2H, m), 2.84–2.76 (1H, m), 2.59–2.46 (1H, m), 2.24 (2H, m), 1.02 (12H, d, J=6.7 Hz)
FAB-MS: Calcd for $C_{43}H_{53}N_6O_8P$, 813 $(M+H)^+$; Found m/z, 813

CEPNT (dA). White foam; overall yield of 70–71%
$^{31}$P-NMR ($CDCl_3$); δ 146.9, 146.81 ppm (ca. $R_p:S_p$, 1:1 mixture)

¹H-NMR (CDCl₃): δ 8.60 (1H, br), 8.58 (1H, s), 8.15 (1H, s), 7.40–7.25 (9H, m), 6.81–6.70 (4H, m), 6.43 (1H, dd, J=2.4, 6.6 Hz), 5.90 (1H, ddt, J=6.5, 10.3, 16.9 Hz), 5.1 (1H, dd, J=1.5, 17.1 Hz), 5.02 (1H, dd, 1.5, J=10 Hz), 4.78 (1H, m), 4.30 (1H, m), 4.20–4.07 (2H, m, 3.74 (6H, s), 3.66–3.54 (2H, m), 3.48 (2H, m), 3.40–3.31 (2H, m), 2.98 (2H, t, J=7.3 Hz), 2.6 (1H, m), 2.53–2.41 (3H, m), 1.16 (12H, d, J=6.6 Hz).
FAB-MS: Calcd for C₄₅H₅₄N₇O₇P, 836.3900 (M+H)⁺; Found, m/z, 836.3899.
CEPNT (dC). Yellow foam; overall yield 72–75%
³¹P-NMR (CDCl₃); δ 147.42, 146.81 ppm (ca. R$_p$:S$_p$, 1:1 mixture)
¹H-NMR (CDCl₃): δ 9.75 (1H,br), 8.20 (1H, d, J=7.3 Hz), 7.43–7.20 (9H, m), 7.24 (1H, d, J=7.3 Hz), 6.75–6.56 (4H, m), 6.22 (1H, t, J=6.1 Hz), 5.8 (1H, ddt, J=6.3, 10.2, 16.6 Hz), 5.05 (1H, dd, J=1.4, 17.1 Hz), 4.98 (1H, dd, J=1.4, 10.3 Hz), 4.60 (1H, m), 4.23–4.12 (3H, m), 3.76 (6H, s), 3.66–3.33 (6H, m), 2.58 (2H, t, J=6.6 Hz), 2.41 (3H, m), 2.3 (1H, m), 1.1 (12H, d, J=6.3 Hz).
FAB-MS; Calcd for C₄₄H₅₄N₅O₈P, 812.3788 (M+J)⁺; Found m/z, 812.3798.
CEPNT (dG). White foam; overall yield of 70–72%
³¹P-NMR (CDCl₃): δ 146.89, 146.83 ppm (ca. R$_p$:S$_p$, 1:1 mixture).
¹H-NMR (CDCl₃): δ 8.04 (1H, br), 7.95 (1H, s), 7.82 (1H, s), 7.43–7.25 (9H, m), 6.82–6.69 (4H, m), 6.25 (1H, dd, J=5.6, 7.8 Hz), 5.70 (1H, m), 5.00 (1H, dd, J=1.5, 17 Hz), 4.95 (1H, dd, J=1.5, 9.5 Hz), 4.70–4.60 (1H, m), 4.15–4.06 (3H, m), 3.65 (6H, s), 3.58–3.20 (6H, m), 2.60 (2H, t, J=6.6 Hz), 2.45 (1H, m), 2.28 (3H, m), 1.09 (12H, d, J=6.4 Hz).
FAB-MS: Calcd for C₄₅H₅₄N₇O₈P, 852.3850 (M+H)⁺, Found m/z, 852.3869.

EXAMPLE 3
Solid phase coupling of nucleoside synthons, introduction of the methyl phosphotriester linkage and removal of base protective groups Methoxy-(MEPNT) 3'-O-(phosphoramidite)-5'-O-(4,4-dimethoxytriphenyl) methyl) [DMT] monomers were coupled in a standard 1H-tetrazole-mediated phosphoramidite coupling reaction to form the dinucleoside phosphites. The dinucleoside phosphites were then oxidized using t-butyl hydroperoxide (1M in toluene) to yield the protected O-methyl phosphotriester, or 3H-benzodithiol-3-one 1,1-dioxide to yield the protected S-methyl phosphotriester. Subsequent exposure to iodine reagent (2% I₂ in pyridine/MeOH, 98/2) at room temperature for 30 minutes completely removed the base protecting groups to give CPG-bound dinucleoside methyl phosphotriesters. Cleavage from the support using anhydrous K₂CO₃ (0.05 M in MeOH) at room temperature for eight hours gave free dinucleoside methyl phosphotriesters in 95–97% yield as R$_p$ and S$_p$ diastereomeric mixtures. The products were analyzed by HPLC (see Iyer et al, Bioorg. Chem. 6: 1 (1995)).

EXAMPLE 4
Synthesis of Chimeric Oligonucleotides

Figure 2:
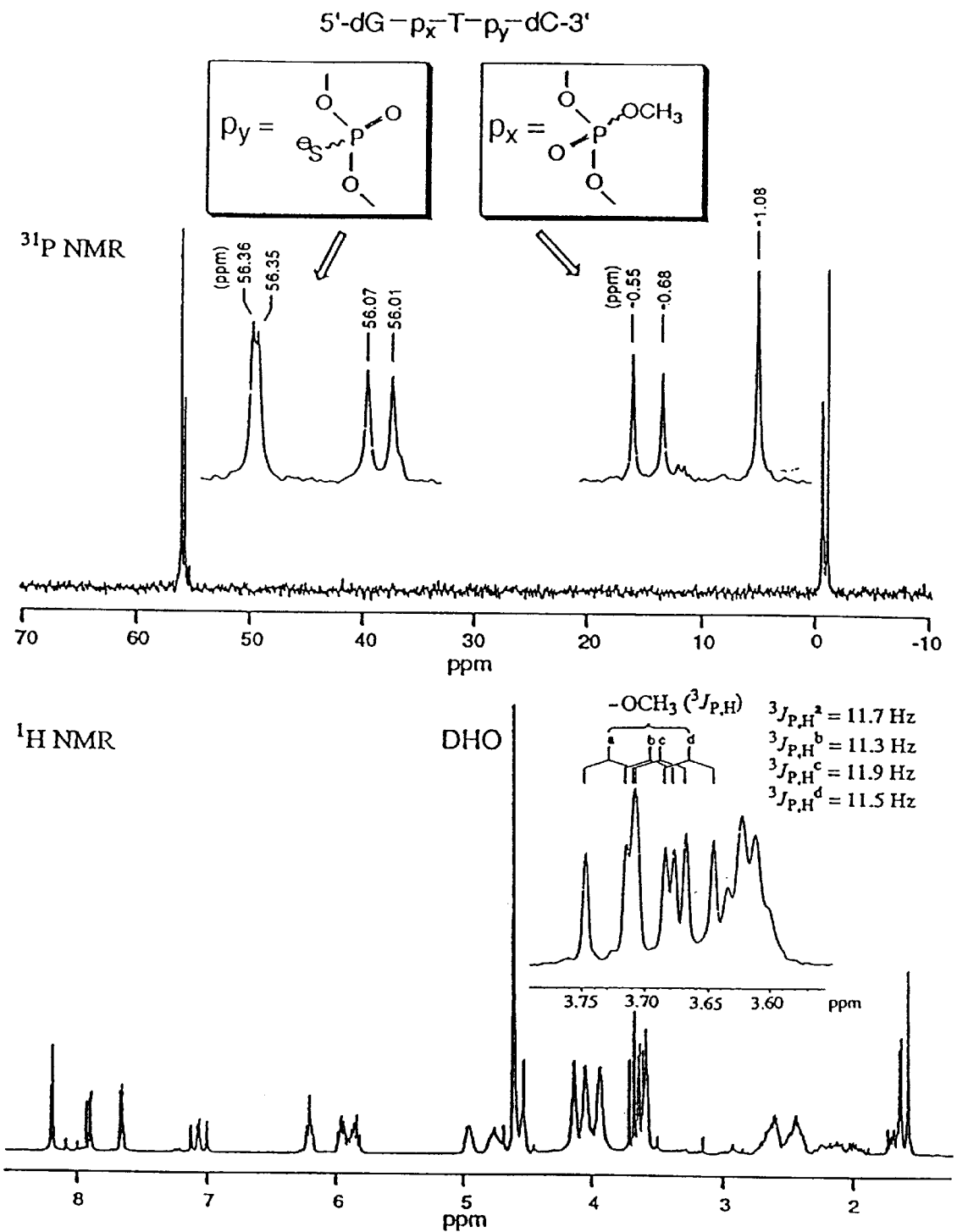
FIG. 2 shows results of $^{31}$P-NMR ($D_2O$, 85% $H_3PO_4$ as external reference) and $^1$H-NMR ($D_2O$) for a trinucleotide chimera according to the invention.

The CEPNT and MEPNT monomers were used to prepare chimeric trinucleotides having one phosphodiester or phosphorothioate internucleoside linkage and one O- or S-methyl phosphotriester internucleoside linkage under conditions as descibed in Example 3. Synthesis was carried out on a solid support using conventional succinyl-linked nucleoside loading. The phosphodiester or phosphorothioate internucleoside linkage was assembled using the CEPNT monomer and the O- or S-methyl phosphotriester internucleoside linkage was assembled using the MEPNT monomer. The trimers thus obtained, a mixture of four diastereomers, were characterized by ³¹P-NMR and ¹H-NMR and by MALDI-TOF mass spectroscopy. Typical NMR results are shown, for one trimer in FIG. 2. In the ³¹P-coupled ¹H-NMR, the OCH₃ protons appeared as four sets of doublets, indicating the presence of the four diastereomers. The MALDI-TOF mass spectrum revealed the expected molecular ion at 911.7 (Na⁺ form) for the species containing the phosphorothioate and S-methylphosphotriester linkages.

Figure 3:
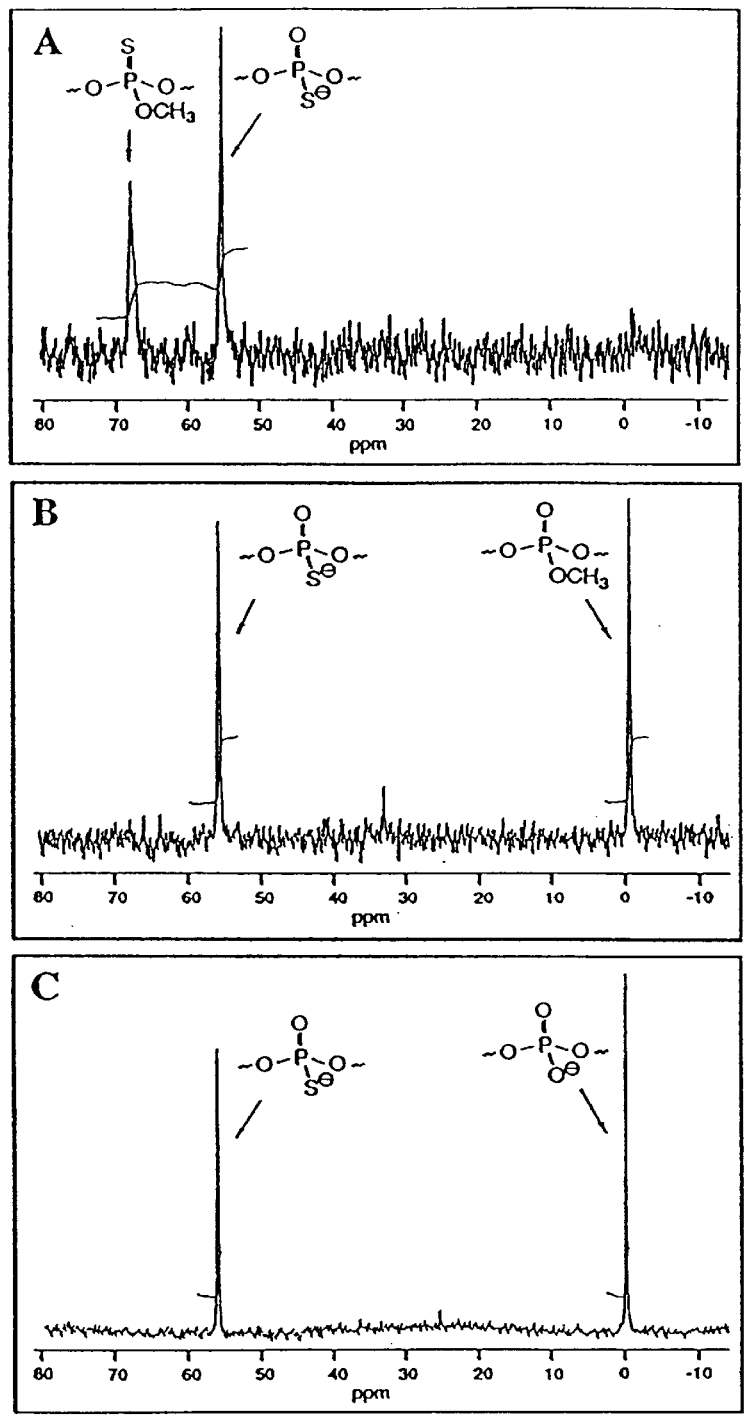
FIG. 3 shows results of $^{31}$P-NMR for two nonanucleotide chimeras according to the invention (panels A and B), and for a phosphodiester-phosphorothioate chimera of identical sequence (panel C).
Figure 4:
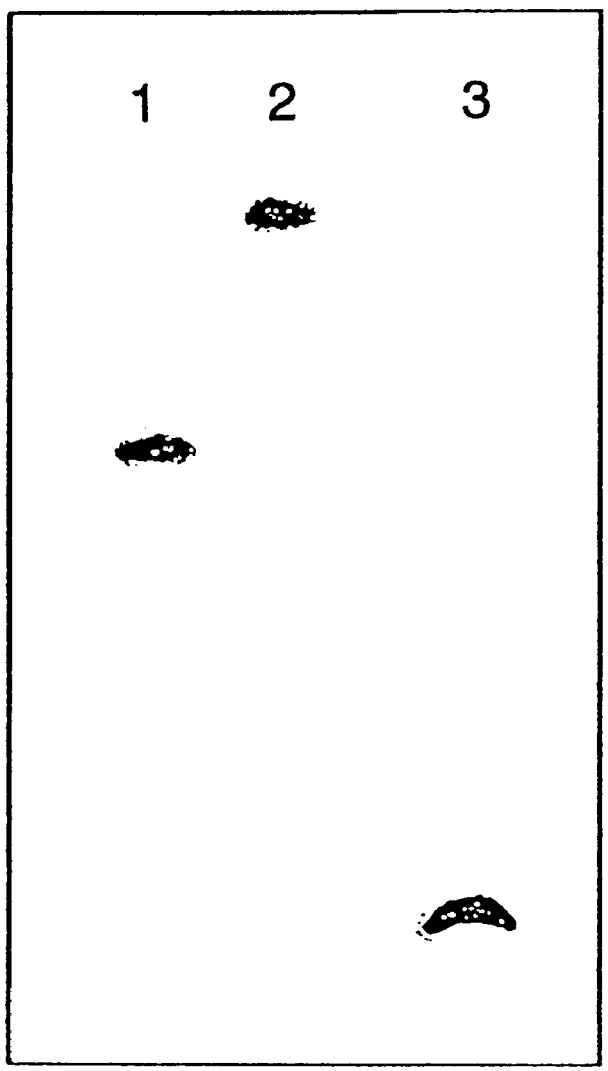
FIG. 4 shows results of polyacrylamide gel electrophoresis for two nonanucleotide chimeras according to the invention (first two lanes), and for a phosphodiester-phosphorothioate chimera of identical sequence (last lane).

This strategy was extended to the synthesis of support-bound nonanucleotide chimeras incorporating four phosphorothioate internucleotide linkages and either four S- or O-methylphosphotriester internucleotide linkages. In each case, ³¹P-NMR analysis proved that the methylphosphotriester and phosphorothioate segments were present in the correct relative proportion, as shown, for example, in FIG. 3. In addition, these chimeras exhibited slower mobility on polyacrylamide gel electrophoresis than a phosphodiester-phosphororthioate chimera of identical sequence, as shown in FIG. 4. These results demonstrate that the mild deprotection conditions according to the invention allow the synthesis of any chimeric oligonucleotide containing these base-sensitive internucleotide linkages.

EXAMPLE 5
Relative nuclease resistance of oligonucleotides containing methyl phosphotriester linkages Oligonucleotides containing either all methyl phosphotriester internucleoside linkages or a mixture of methyl phosphotriester internucleoside linkages and phosphorothioate or phosphodiester internucleoside linkages in various chimeric configurations were synthesized according to Example 3 or 4. Oligonucleotide phosphodiesters and phosphorothioates were synthesized according to standard procedures.

To test the relative nuclease resistance of these oligonucleotides the oligonucleotides were treated with snake venom phosphodiesterase (SVPD). About 0.2 A₂₆₀ units of oligonucleotide was dissolved in 500 microliters buffer (40 mM NH₄CO₃, pH 7.0, 20 mM MgCl₂) and mixed with 0.1 units SVPD. The mixture was incubated at 37° C. for 420 minutes. After 0, 200 and 420 minutes, 165 microliter aliquots were removed and analyzed using ion exchange HPLC. Oligonucleotides containing methyl phosphotriester internucleoside linkages exhibited greater nuclease resistance than oligonucleotides containing exclusively phosphodiester or phosphorothioate internucleoside linkages.

EXAMPLE 6
Duplex stability of oligonucleotides containing methyl phosphotriester internucleoside linkages Oligonucleotides containing either all methyl phosphotriester internucleoside linkages or a mixture of methyl phosphotriester internucleoside linkages and phosphorothioate or phosphodiester internucleoside linkages in various chimeric configurations were synthesized using the process described in Example 3 or 4. Oligonucleotide phosphodiesters and phosphorothioates were synthesized according to standard procedures. The oligonucleotides are tested for their ability to form duplexes with complementary oligodeoxyribonucleotides and oligoribonucleotides. In separate reactions, each oligonucleotide is mixed with an equivalent quantity (0.2 A₂₆₀ units) of its complementary oligonucleotide in 150 mM NaCl, 10 mM Na₂PO₄, 1 mM EDTA (pH 7.0). The mixture is heated to 85° C. for 5 minutes, then cooled to 30° C. The temperature is then increased from 30° C. to 80° C. at a rate of 1° C. per minute and A₂₆₀ is recorded as a function of temperature. Oligonucleotides according to

EXAMPLE 7
Inhibition of HIV-1 by oligonucleotides containing methyl phosphotriester internucleoside linkages the invention are expected to form duplexes with complementary oligodeoxyribonucleotides or oligoribonucleotides at temperatures well above physiological temperatures.

Oligonucleotides containing either all methyl phosphotriester internucleoside linkages or a mixture of methyl phosphotriester internucleoside linkages and phosphorothioate or phosphodiester internucleoside linkages in various chimeric configurations are synthesized according to the process described in Examples 3 or 4. Oligonucleotide phosphodiesters and phosphorothioates are synthesized according to standard procedures. The oligonucleotides have a previously described sequence that is complementary to a portion of the gag gene of HIV-1 (see Agrawal and Tang, Antisense Research and Development 2: 261–266(1992)).

Oligonucleotides are tested for their ability to inhibit HIV-1 in a tissue culture system. H9 lymphocytes are infected with HIV-1 virions (0.01–0.1 $TCID_{50}$/cell) for one hour at 37° C. After one hour, unadsorbed virions are washed away and the infected cells are divided among wells of 24 well plates. To the infected cells, an appropriate concentration (from stock solution) of oligonucleotide is added to obtain the required concentration (0.1–10 micromolar) in 2 ml media. The cells are then cultured for four days. At the end of four days, inhibition of HIV-1 is assessed by observing or measuring reductions in syncytium formation, p24 expression and reverse transcriptase activity. All of the tested oligonucleotides according to the invention are expected to show significant reductions in these parameters without significant cytotoxicity.

What is claimed is:

1. A process for synthesizing an oligonucleotide containing from one to all methylphosphotriester internucleoside linkages, the process comprising condensing in the presence of 1H-tetrazole a methoxy-3'-O-(phosphoramidite)-5'-O-(4,4'-dimethoxytriphenyl) methyl nucleoside with another nucleoside, wherein at least one of the nucleosides has a nucleoside base protective group having the general structure II:

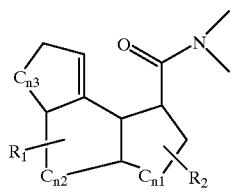

where $n_1$, $n_2$, and $n_3$ are independently 0–10, the ring structures shown may be aromatic or heterocyclic, the nitrogen displayed is the protected amino moiety of the nucleoside base, and $R_1$ and $R_2$ are independently hydrogen, or an alkyl, aralkyl, ether, hydroxy, nitrile, nitro, ester, carboxyl, or aldehyde group.

2. The process according to claim 1, wherein the internucleotidic phosphite linkage is oxidized using t-butyl hydroperoxide to yield an O-methyl phosphotriester linkage.

3. The process according to claim 2, wherein the chemoselective removing agent is a halogen in water, or in pyridine/ROH, wherein R is an alkyl, aralkyl or aryl group having 1–10 carbon atoms.

4. The process according to claim 2, wherein the halogen is $Cl_2$ or $Br_2$.

5. The process according to claim 2, wherein $n_1$, $n_2$ and $n_3$ are each 0.

6. The process according to claim 2, wherein the chemoselective removing agent is a halogen in water, or in pyridine/ROH, wherein R is an alkyl, aralkyl or aryl group having 1–10 carbon atoms.

7. The process according to claim 2, wherein the halogen is $Cl_2$ or $Br_2$.

8. The process according to claim 1, wherein the internucleotidic phosphite linkage is oxidized using 3H-benzodithiol-3-one 1,1-dioxide to yield an S-methyl phosphotriester linkage.

9. The process according to claim 8, wherein the chemoselective removing agent is a halogen in water, or in pyridine/ROH, wherein R is an alkyl, aralkyl or aryl group having 1–10 carbon atoms.

10. The process according to claim 8, wherein the halogen is $Cl_2$ or $Br_2$.

11. The process according to claim 8, wherein $n_1$, $n_2$ and $n_3$ are each 0.

12. The process according to claim 8, wherein the chemoselective removing agent is a halogen in water, or in pyridine/ROH, wherein R is an alkyl, aralkyl or aryl group having 1–10 carbon atoms.

13. The process according to claim 8, wherein the halogen is $Cl_2$ or $Br_2$.

14. A process for synthesizing an oligonucleotide containing from one to all methylphosphotriester internucleoside linkages, the process comprising condensing in the presence of 1H-tetrazole a methoxy-3'-O-(phosphoramidite)-5'-O-(4,4'-dimethoxytriphenyl) methyl nucleoside with another nucleoside, wherein at least one of the nucleosides has a N-pent-4-enoyl nucleoside base protective group.

* * * * *